United States Patent [19]
Riebel et al.

[11] 4,392,882
[45] Jul. 12, 1983

[54] N-N-BIS(HALOACYL)-DIAZA-CYCLOALKANES FOR PROTECTING PLANTS FROM HERBICIDE DAMAGE

[75] Inventors: Hans-Jochem Riebel, Wuppertal; Ludwig Eue, Leverkusen; Wilfried Faust, Odenthal, all of Fed. Rep. of Germany

[73] Assignee: Bayer Aktiengesellschaft, Leverkusen, Fed. Rep. of Germany

[21] Appl. No.: 166,412

[22] Filed: Jul. 7, 1980

[30] Foreign Application Priority Data

Jul. 26, 1979 [DE] Fed. Rep. of Germany ....... 2930452

[51] Int. Cl.$^3$ ............................................. A01D 25/32
[52] U.S. Cl. ........................................... 71/92; 71/90; 71/100; 71/118
[58] Field of Search ............................................. 71/92

[56] References Cited

U.S. PATENT DOCUMENTS 3,898,338  8/1975  Martin et al. ....................... 424/250

FOREIGN PATENT DOCUMENTS 2218097 11/1972 Fed. Rep. of Germany .
2328870  1/1975 Fed. Rep. of Germany .

OTHER PUBLICATIONS

J. Med. Chem. II, 621–622 (1973).
Rocz. Chem. 47, 1277–1280, 1937–1942 (1973).
Rocz. Chem. 38, 229–235 (1964).
J. Agricultural and Food Chemistry 26, 137–140 (1978).

*Primary Examiner*—Catherine L. Mills
*Attorney, Agent, or Firm*—Felfe & Lynch

[57] ABSTRACT

The use of N,N'-bis-(haloacyl)-diaza-cycloalkanes of the general formula

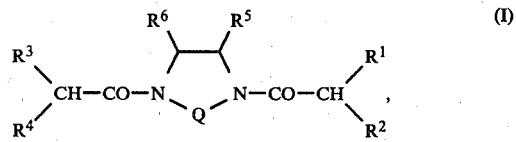

in which
  $R^1$ represents alkyl or halogen,
  $R^2$ represents halogen,
  $R^3$ represents alkyl or halogen,
  $R^4$ represents halogen,
  $R^5$ represents hydrogen or alkyl with 1 to 4 carbon atoms,
  $R^6$ represents hydrogen or alkyl with 1 to 4 carbon atoms and
  Q represents an alkylene chain which has 2 or 3 carbon atoms in the alkylene chain and is optionally monosubstituted or polysubstituted by alkyl with 1 to 4 carbon atoms, as antidotes for protecting crop plants from damage by herbicides.

15 Claims, No Drawings

N-N-BIS(HALOACYL)-DIAZA-CYCLOALKANES FOR PROTECTING PLANTS FROM HERBICIDE DAMAGE

This invention relates to a method of protecting crop plants from damage by herbicides, by use of N,N'-bis-(haloacyl)-diaza-cycloalkanes as antidotes. More specifically, the invention relates to providing such antidotes for herbicidally active thiolcarbamates and acetanilides and to new active compound combinations which consist of certain N,N'-bis-(haloacyl)-diaza-cyacloalkanes and such herbicidally active thiolcarbamates or acetanilides.

By "antidote" ("safener") there are to be understood, in the present connection, substances which are capable of specifically antagonizing harmful effects of herbicides on crop plants, that is to say of protecting the crop plants without thereby noticeably influencing the herbicidal action on the weeds to be combated.

It is known that when certain thiolcarbamates and acetanilides are used for combating weeds in maize and other crops, they cause damage, to a greater or lesser extent, to the crop plants. It is also known that such compounds as, for example, N-dichloroacetyl-2-ethyl-piperidine and N-dichloroacetyl-cis/trans-decahydroquinoline are suitable compounds for reducing damage caused by crop plants by thiolcarbamates or acetanilides (see DE-OS (German Published Specification) 2,218,097). However, the activity of these substances as antidotes is not always complete satisfactory.

It is also known that 1,4-bis-(haloacyl)-piperazines, such as 1,4-bis-(α-chloropropionyl)-piperazine or 1,4-bis-(α-bromo-propionyl)-piperazine, have cytostatic properties (see J. Med. Chem. 11 (1968), 621–622). Moreover, it is known from the literature that certain 1,4-bis-(haloacyl)-piperazines can be employed as intermediate products for the preparation of substances with a mucolytic action (see U.S. Pat. No. 3,898,338).

It has now been found that the N,N'-bis-(haloacyl)-diazacycloalkanes, some of which are known, of the general formula

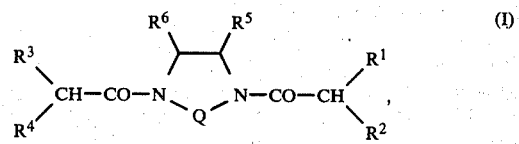

in which
R$^1$ represents alkyl or halogen,
R$^2$ represents halogen,
R$^3$ represents alkyl or halogen,
R$^4$ represents halogen,
R$^5$ represents hydrogen or alkyl with 1 to 4 carbon atoms,
R$^6$ represents hydrogen or alkyl with 1 to 4 carbon atoms and
Q represents an alkylene chain which has 2 or 3 carbon atoms in the alkylene chain and is optionally monosubstituted or polysubstituted by alkyl with 1 to 4 carbon atoms,
are outstandingly suitable for protecting crop plants from damage by herbicidally active thiolcarbamates or by herbicidally active acetanilides.

Accordingly, the present invention provides an antidote composition containing as active ingredient a compound of the formula (I) in admixture with a solid diluent or carrier or in admixture with a liquid diluent or carrier containing a surface-active agent.

The present invention also provides a method of protecting crop plants from damage by herbicidally active thiolcarbamates or herbicidally active acetanilides, in which there is applied to the plants, or to a habitat thereof, a compound of the formula (I) alone or in the form of a composition containing as active ingredient a compound of the formula (I) in admixture with a diluent or carrier.

It has furthermore been found that the new active compound combinations consisting of an N,N'-bis-(haloacyl)-diaza-cycloalkane of the formula (I) and at least one herbicidally active thiolcarbamate and/or at least one herbicidally active acetanilide are outstandingly suitable for selectively combating weeds in crops of useful plants.

The present invention also provides a herbicidal composition that contains as active ingredients (1) a compound of the formula (I) and (2) at least one herbicidally active compound selected from thiolcarbamates and acetanilides, alone or in admixture with a solid or liquid diluent or carrier.

The present invention also provides a method of combating weeds, in which there is applied to the weeds, or to a habitat thereof, a herbicidal composition according to the present invention.

Surprisingly, herbicidal damage to crop plants by thiolcarbamates or by acetanilides can be better suppressed if N,N'-bis-(haloacyl)-diaza-cycloalkanes of the formula (I) are also used than if the known compounds N-dichloroacetyl-2-ethyl-piperidine and N-dichloroacetyl-cis/trans-decahydroquinoline, which are chemically similar substances of the same type of action, are used. Moreover, it was not to be expected that the active compound combinations according to the invention have better selective herbicidal properties than active compound combinations which consist of at least one herbicidally active thiolcarbamate or at least one herbicidally active acetanilide and N-dichloroacetyl-2-ethyl-piperidine which is known as an antidote, or N-dichloroacetyl-cis/trans-decahydroquinoline, which is also known as an antidote. The use of the substances of the formula (I), which can be employed according to the invention, for the purpose indicated is thus a valuable enrichment of the art.

The formula (I) provides a general definition of the N,N'-bis-(haloacyl)-diaza-cycloalkanes which can be used according to the invention. Preferably, in this formula,
R$^1$ represents straight-chain or branched alkyl with 1 to 4 carbon atoms, chlorine or bromine,
R$^2$ represents chlorine or bromine,
R$^3$ represents straight-chain or branched alkyl with 1 to 4 carbon atoms, chlorine or bromine,
R$^4$ represents chlorine or bromine,
R$^5$ represents hydrogen or alkyl with 1 to 2 carbon atoms,
R$^6$ represents hydrogen or alkyl with 1 or 2 carbon atoms, and
Q represents an alkylene chain which has 2 or 3 carbon atoms and can be mono-substituted or polysubstituted by methyl or ethyl.

Some of the N,N'-bis-(haloacyl)-diaza-cycloalkanes of the formula (I) which can be used according to the invention are known (see U.S. Pat. No. 3,898,338; J. Med. Chem. 11 (1968), 621–622; Rocz. Chem. 47 (1973)

6, 1,277–1,280; Rocz. Chem. 38 (1964), 229–234 and Rocz. Chem. 47 (1973), 1,937–1,942). The substances of the formula (I) which have not hitherto been described in the literature can be prepared in a simple manner by processes which are known in principle. Thus, N,N′-bis-(haloacyl)-diaza-cycloalkanes of the formula (I) are obtained by (a) reacting diaza-cycloalkanes of the general formula

in which $R^5$, $R^6$ and Q have the meanings indicated above, with alkanoyl chlorides of the general formula

in which $R^1$ and $R^2$ have the meanings indicated above, if appropriate in the presence of a diluent and if appropriate in the presence of an acid-binding agent, or (b) reacting N-haloacyl-diaza-cycloalkanes of the general formula

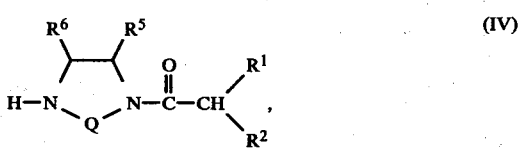

in which $R^1$, $R^2$, $R^5$, $R^6$ and Q have the meanings indicated above, with alkanoyl chlorides of the general formula

in which $R^3$ and $R^4$ have the meanings indicated above, if appropriate in the presence of a diluent and if appropriate in the presence of an acid-binding agent.

The formula (II) provides a general definition of the diaza-cycloalkanes required as starting substances in carrying out process (a). In this formula, $R^5$, $R^6$ and Q preferably represent those radicals which have already been mentioned as preferred in connection with the description of the N,N′-bis-(haloacyl)-diaza-cycloalkanes of the formula (I).

The diaza-cycloalkanes of the formula (II) are known, or they can be prepared by processes which are known in principle.

The formula (IV) provides a general definition of the N-haloacyl-diaza-cycloalkanes required as starting substances in carrying out process (b). In this formula, $R^1$, $R^2$, $R^5$, $R^6$ and Q preferably represent those radicals which have already been mentioned as preferred in connection with the description of the N,N′-bis-(haloacyl)-diaza-cycloalkanes of the formula (I).

The N-haloacyl-diaza-cycloalkanes of the formula (IV) are known, or they can be prepared in a simple manner by processes which are known in principle. Thus, the substances concerned can be obtained, for example, if, in the reaction of process (a), which is described, the diazacycloalkane of the formula (II) is reacted with the stoichiometric amount of alkanoyl chloride of the formula (IIIa) calculated for simple haloacetylation.

The formulae (IIIa) and (IIIb) provide general definitions of the alkanoyl chlorides also required as starting substances in processes (a) and (b). In these formulae, $R^1$, $R^2$, $R^3$ and $R^4$ preferably represent those radicals which have already been mentioned as preferred in connection with the description of the N,N′-bis-(haloacyl)-cycloalkanes of the formula (I).

The alkanoyl chlorides of the formulae (IIIa) and (IIIb) are known, or they can be prepared in a simple manner by processes which are known in principle (see DE-OS (German Published Specification) 2,218,097).

Processes (a) and (b) for the preparation of the N,N′-bis-(haloacyl)-diaza-cycloalkanes of the formula (I) are preferably carried out in the presence of a diluent. Diluents which can be used here are water and inert organic solvents. These solvents include, as preferences, ketones, such as diethyl ketone and methyl isobutyl ketone; nitriles, such as propionitrile and acetonitrile; ethers, such as tetrahydrofuran and dioxan; aliphatic and aromatic hydrocarbons, such as petroleum ether, benzene, toluene or xylene; halogenated hydrocarbons, such as methylene chloride, carbon tetrachloride, chloroform or chlorobenzene; esters, such as ethyl acetate; and formamides, such as, in particular, dimethylformamide.

Possible acid-binding agents in the preparation of the N,N′-bis-(haloacyl)-diaza-cycloalkanes of the formula (I), both by process (a) and by process (b), are any of the customary acid acceptors. These include, as preferences, alkali metal hydroxides, such as sodium hydroxide and potassium hydroxide, alkali metal carbonates, such as sodium carbonate, potassium carbonate and sodium bicarbonate, and lower tertiary amines, such as triethylamine, dimethylbenzylamine, pyridine and diazabicyclooctane. However, diaza-cyclo-alkane of the formula (II) (process (a)) or N-(haloacyl)-diaza-cycloalkane of the formula (IV) (process (b)) employed in excess can also simultaneously function as the acid-binding agent. In these cases, it is not necessary to add separately an additional acid-binding agent.

The reaction temperatures can be varied within a substantial range both in process (a) and in process (b). In general, the reaction is in each case carried out at temperatures between 0° C. and 100° C., preferably between 10° C. and 80° C.

In carrying out process (a), 2 to 3 moles of alkanoyl chloride of the formula (IIIa) and, if appropriate, 1 mole of acid-binding agent are preferably employed per mole of diaza-cycloalkane of the formula (II). Isolation of the reaction products is effected by customary methods. In generally, a procedure is followed in which the precipitate obtained, if appropriate after first adding water to the reaction mixture, is filtered off, washed and recrystallized.

In carrying out process (b), 1 mole of alkanoyl chloride of the formula (IIIb) and, if appropriate, 1 mole of acid-binding agent are preferably employed per 1 mole of N-haloacyl-diaza-cycloalkane of the formula (IV). Isolation of the reaction products is effected by customary methods. In general, a procedure is followed such as has already been described in connection with process (a).

As already mentioned, the N,N'-bis-(haloacyl)-cycloalkanes of the formula (I) which can be used according to the invention are suitable for protecting crop plants from damage by herbicidally active thiol-carbamates or acetanilides, without noticeably influencing the herbicidal action of these compounds.

The N,N'-bis-(haloacyl)-diaza-cycloalkanes of the formula (I) can preferably be used for protecting crop plants from damage by herbicidally active thiol-carbamates of the general formula

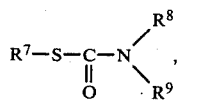
(V)

in which
  $R^7$ represents lower alkyl, benzyl, chlorobenzyl or alkoxybenzyl and
  $R^8$ and $R^9$ independently of one another represent alkyl with 2 to 4 carbon atoms or cyclohexyl, or
  $R^8$ and $R^9$, together with the adjacent nitrogen atom, represent a five-membered to seven-membered heterocyclic ring,
and for protecting crop plants from damage by herbicidally active acetanilides of the general formula

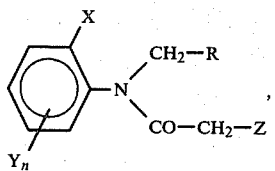
(VI)

in which
  R represents an optionally substituted N-containing heterocyclic radical,
  X and Y are identical or different and represent alkyl,
  Z represents halogen and
  n represents 0, 1 or 2,
and herbicidally active acid addition salts and metal salt complexes thereof, and of the general formula

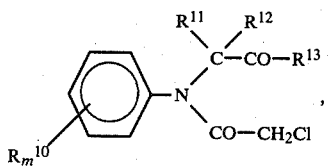
(VII)

in which
  $R^{10}$ represents alkyl, halogen, haloalkyl, alkylthio, alkylsulphonyl, aminosulphonyl, cyano, or nitro,
  $R^{11}$ and $R^{12}$ are identical or different and represent hydrogen, alkyl, halogen, haloalkyl or optionally substituted phenyl,
  $R^{13}$ represents alkyl or optionally substituted phenyl and
  m represents 0 or an integer from 1 to 5,
and of the general formula

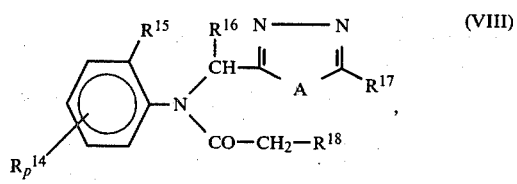
(VIII)

in which
  A represents oxygen, sulphur or the grouping $>NR^{19}$,
  $R^{16}$ represents hydrogen or alkyl,
  $R^{17}$ represents hydrogen, alkyl, haloalkyl, alkenyl, alkynyl, cycloalkyl, halogen, optionally substituted aryl or aralkyl or the grouping $-OR^{20}$, $-SR^{20}$ or $-NR^{19}R^{20}$,
  $R^{19}$ represents hydrogen, alkyl or optionally substituted aryl,
  $R^{20}$ represents hydrogen, alkyl, haloalkyl, alkenyl, alkynyl, cycloalkyl or optionally substituted aralkyl,
  $R^{14}$ represents alkyl,
  $R^{15}$ represents alkyl or halogen,
  $R^{18}$ represents halogen and
  p represents 0, 1 or 2,
and of the formula

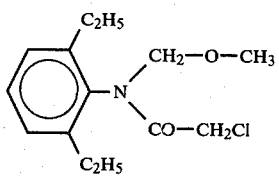
(IX)

and of the formula

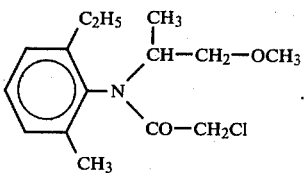
(X)

Specific examples of thiolcarbamates of the formula (V) which may be mentioned are: S-ethyl N-N-dipropylthiocarbamate, S-ethyl N,N-diisobutylthiocarbamate, S-propyl N-butyl-N-ethylthiocarbamate, S-propyl N,N-diisopropylthiocarbamate, S-ethyl N,N-diethylthiocarbamate, S-ethyl N-ethyl-N-cyclohexylthiocarbamate, S-ethyl hexahydroazepine-1-thiocarbamate, S-p-methoxybenzyl N,N-diethylthiocarbamate, S-p-chlorobenzyl N,N-diethylthiocarbamate, S-benzyl N,N-diethylthiocarbamate, S-benzyl N,N-di-sec.butylthiocarbamate and S-propyl N-ethyl-N-butylthiocarbamate.

The thiolcarbamates of the formula (V) and their herbicidal activity are already known (see U.S. Pat. Nos. 2,913,327; 3,037,853; 3,175,897; 3,185,720; 3,198,786 and 3,582,314).

In the formula (VI) R preferably represents an optionally substituted pyrazol-1-yl, imidazol-1-yl, 1,2,4-triazol-1-yl, 1,2,3-triazol-1-yl, 1,3,4-triazol-1-yl, 1,2,3,4-tetrazol-1-yl or pyrrol-1-yl radical. Preferred substituents are halogen (especially fluorine, chlorine and bromine) and alkyl with 1 to 4 carbon atoms. X and Y are identical or different and preferably represent straight-chain or branched alkyl with 1 to 4 carbon atoms. Z preferably represents the halogens chlorine and bromine and the index n represents 0, 1 or 2.

Specific examples of acetanilides of the formula (VI) which may be mentioned are: 2-methyl-6-ethyl-N-(pyrazol-1-yl-methyl)-chloroacetanilide, 2,6-diethyl-N-(pyrazol-1-yl-methyl)-chloroacetanilide, 2,6-diethyl-N-(1,2,4-triazol-1-yl-methyl)-chloroacetanilide, 2,6-dimethyl-N-(1,2,4-trazol-1-yl-methyl)-chloroacetanilide, 2-methyl-N-(pyrazol-1-yl-methyl)-chloroacetanilide, 2,5-dimethyl-N-(pyrazol-1-yl-methyl)-chloroacetanilide, 2,3-dimethyl-N-(pyrazol-1-yl-methyl)-chloroacetanilide, 2-methyl-6-ethyl-N-(pyrazol-1-yl-methyl)-chloroacetanilide hydrochloride, 2,6-diethyl-N-(pyrazol-1-yl-methyl)-chloroacetanilide hydrochloride, 2,6-diethyl-N-[(3,5-dimethyl-pyrazol-1-yl)-methyl]-chloroacetanilide, 2,6-diethyl-N-[(3-chloro-1,2,4-triazolyl)-methyl]-chloroacetanilide, 2-methyl-6-ethyl-N-[(3,5-dimethyl-pyrazol-1-yl)-methyl]-chloroacetanilide, 2-tert.-butyl-N-(pyrazol-1-yl-methyl)-chloroacetanilide, 2-methyl-6-ethyl-N-[(3-bromo-5-methyl-pyrazol-1-yl)-methyl]-chloroacetanilide, 2-methyl-6-ethyl-N-[(3-chloro-1,2,4-triazolyl)-methyl]-chloroacetanilide and 2,6-diethyl-N-[(4-chloro-pyrazol-1-yl)-methyl]-chloroacetanilide.

Further preferred acetanilides of the formula (VI) are listed in the preparative examples.

The acetanilides of the formula (VI) and their herbicidal activity, and herbicidally active acid addition salts and metal salt complexes thereof are already known (see DE-OS (German Published Specification) 2,648,008 and DE-OS (German Published Specification) 2,704,281).

In the formula (VII), $R^{10}$ preferably represents straight-chain or branched alkyl with 1 to 6 (especially 1 to 4) carbon atoms, halogen (especially fluorine, chlorine and bromine), haloalkyl with up to 3 carbon atoms and up to 5 identical or different halogen atoms (preferred halogens being fluorine and chlorine, and trifluoromethyl being mentioned as an example), alkylthio or alkylsulphonyl with in either case 1 to 4 carbon atoms in the alkyl part, aminosulphonyl, cyano or nitro. $R^{11}$ and $R^{12}$ are identical or different and preferably represent hydrogen, straight-chain or branched alkyl with 1 to 4 carbon atoms, halogen (especially fluorine, chlorine or bromine), haloalkyl with up to 3 carbon atoms and up to 5 identical or different halogen atoms (preferred halogens being fluorine and chlorine), or optionally mono-substituted or polysubstituted phenyl, preferred substituents being those radicals mentioned for $R^{10}$. $R^{13}$ preferably represents straight-chain or branched alkyl with 1 to 6 (especially 1 to 4) carbon atoms or optionally monosubstituted or polysubstituted phenyl, preferred substituents being selected from alkyl with 1 to 4 carbon atoms, halogen (especially fluorine, chlorine and bromine), haloalkyl with up to 3 carbon atoms and up to 5 identical or different halogen atoms (especially fluorine or chlorine atoms, trifluoromethyl being mentioned as an example), alkoxy, alkylthio and alkylsulphonyl with in each case 1 to 4 carbon atoms, aminosulphonyl, cyano, nitro and phenyl and phenoxy, in either case optionally substituted by chlorine. The index m preferably represents 1, 2 or 3.

Specific examples of acetanilides of the formula (VII) which may be mentioned are: 2,6-dimethyl-N-(benzoyl-methyl)-chloroacetanilide, 2,6-dimethyl-N-(4-chloro-benzoyl-methyl)-chloroacetanilide and 2-methyl-6-ethyl-N-(benzoyl-methyl)-chloroacetanilide.

Further preferred acetanilides of the formula (VII) are listed in the preparative examples.

The acetanilides of the formula (VII) and their herbicidal activity are already known (compare DE-OS (German Published Specification) 2,726,253).

In the formula (VIII), A preferably represents oxygen, sulphur or the grouping —$NR^{19}$, wherein $R^{19}$ represents hydrogen, straight-chain or branched alkyl with 1 to 4 carbon atoms or aryl with 6 to 10 carbon atoms (especially phenyl) it being possible for the aryl radical to carry one or more substituents selected from halogen, alkyl with 1 to 4 carbon atoms, alkoxy with 1 or 2 carbon atoms, alkylthio with 1 or 2 carbon atoms, cyano, nitro and haloalkyl with up to 2 carbon atoms and up to 5 identical or different halogen atoms (preferred halogens being fluorine and chlorine). $R^{16}$ preferably represents hydrogen or methyl. $R^{17}$ in the formula (VIII) preferably represents hydrogen, straight-chain or branched alkyl with 1 to 4 carbon atoms, haloalkyl with up to 3 carbon atoms and up to 5 identical or different halogen atoms (preferred halogens being fluorine and chlorine, and trifluoromethyl being mentioned as an example), alkenyl or alkynyl with 2 to 4 carbon atoms, cycloalkyl with 5 to 7 carbon atoms or halogen (especially fluorine, chlorine or bromine). $R^{17}$ furthermore preferably represents aryl with 6 to 10 carbon atoms (especially phenyl), it being possible for the aryl radical to carry one or more substituents selected from halogen, alkyl with 1 to 4 carbon atoms, alkoxy with 1 or 2 carbon atoms, alkylthio with 1 or 2 carbon atoms, cyano, nitro and haloalkyl with up to 2 carbon atoms and up to 5 identical or different halogen atoms (preferred halogens being fluorine or chlorine, and trifluoromethyl being mentioned as a specific example of haloalkyl). $R^{17}$ furthermore preferably represents aralkyl with 6 to 10 carbon atoms in the aryl part and 1 to 4 carbon atoms in the alkyl part (especially benzyl), it being possible for the aryl part of the aralkyl radical to carry one or more substituents selected from halogen, alkyl with 1 to 4 carbon atoms, alkoxy with 1 or 2 carbon atoms, alkylthio with 1 or 2 carbon atoms, cyano, nitro and haloalkyl with up to 2 carbon atoms and up to 5 identical or different halogen atoms (preferred halogens being fluorine or chlorine, and trifluoromethyl being mentioned as a specific example of haloalkyl). $R^{17}$ also represents the grouping —$OR^{20}$, —$SR^{20}$ or —$NR^{19}R^{20}$, wherein $R^{19}$ preferably represents those radicals which have already been mentioned above as preferred for this radical, and $R^{20}$ in these groupings represents hydrogen, straight-chain or branched alkyl with 1 to 4 carbon atoms, haloalkyl with 1 to 3 carbon atoms and up to 5 identical or different halogen atoms (preferred halogens being fluorine and chlorine, and trifluoromethyl being mentioned as an example), alkenyl or alkynyl with 2 to 4 carbon atoms, cycloalkyl with 5 to 7 carbon atoms or aralkyl with 6 to 10 carbon atoms in the aryl part and 1 to 4 carbon atoms in the alkyl part (especially benzyl), it being possible for the aryl part of the aralkyl radical to carry one or more substituents selected from halogen, alkyl with 1 to 4 carbon atoms, alkoxy with 1 or 2 carbon atoms, alkylthio with 1 or 2 carbon atoms, cyano, nitro and haloalkyl with up to 2 carbon atoms and up to 5 identical or different halogen atoms (preferred halogens being fluorine or chlorine, and trifluoromethyl being mentioned as a specific example of haloalkyl). In the formula (VIII), $R^{14}$ preferably represents straight-chain or branched alkyl with 1 to 4 carbon atoms. $R^{15}$ in the formula (VIII) preferably represents straight-chain or branched alkyl with 1 to 4 carbon atoms, fluorine, chlorine or bromine. $R^{18}$ in the formula (VIII) preferably represents chlorine, bromine or iodine. The index p represents 0, 1 or 2.

Specific examples of acetanilides of the formula (VIII) which may be mentioned are: 2,6-diethyl-N-[(2-methyl-1,3,4-oxadiazol-5-yl)-methyl]-chloroacetanilide, 2,6-dimethyl-N-[(2-methyl-1,3,4-oxadiazol-5-yl)-methyl]-chloroacetanilide, 2-ethyl-6-methyl-N-[(2-methyl-1,3,4-oxadiazol-5-yl)-methyl]-chloroacetanilide and 2-tert.-butyl-N-[(2-methyl-1,3,4-oxadiazol-5-yl)-methyl]-chloroacetanilide.

Further preferred acetanilides of the formula (VIII) are listed in the preparative examples.

The acetanilides of the formula (VIII) and their herbicidal activity have not hitherto been described in the literature. They can be prepared in a simple manner. Thus, acetanilides of the formula (VIII) are obtained by reacting N-azolyl-alkyl-anilides of the general formula

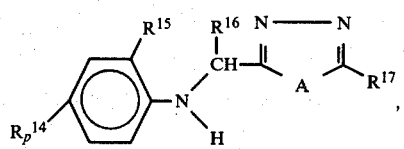
(XI)

in which
$R^{14}$, $R^{15}$, $R^{16}$, $R^{17}$, A and p have the meanings indicated above,
with haloacetic acid chlorides or anhydrides of the general formula

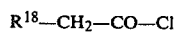 (XIIa)

or

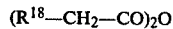 (XIIb), in which
$R^{18}$ has the meaning indicated above,
in the presence of a diluent and if appropriate in the presence of an acid-binding agent.

If 2,6-diethyl-N-(3-methylthio-4-methyl-1,2,4-triazol-5-yl-methyl)-aniline and chloroacetyl chloride are used as starting substances, the course of the reaction in the process for the preparation of the acetanilides of the formula (VIII) can be represented by the following equation:

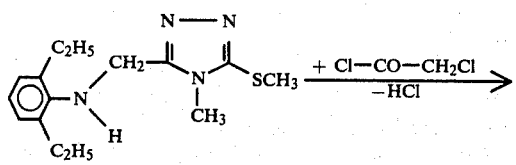

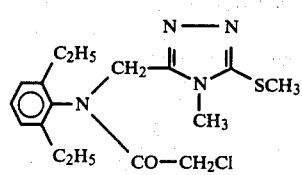

The formula (XI) provides a general definition of the N-azolylalkylanilines required as starting substances in carrying out the process for the preparation of the acet-anilides of the formula (VIII). In this formula, $R^{14}$, $R^{15}$, $R^{16}$, $R^{17}$, A and p preferably have those meanings which have already been mentioned as preferred in connection with the description of the acetanilides of the formula (VIII).

The N-azolylalkylanilines of the formula (XI) required as starting substances in the process for the preparation of the acetanilides of the formula (VIII) have not hitherto been disclosed in the literature. However, they can be prepared in a simple manner by several process. Thus, N-azolyl-alkylanilines of the formula (XI) are obtained by
(c) reacting anilines of the general formula

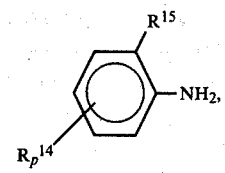
(XIII)

in which
$R^{14}$, $R^{15}$ and p have the meanings indicated above, with azole derivatives of the general formula

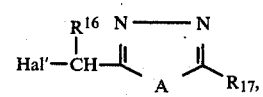
(XIV)

in which
A, $R^{16}$ and $R^{17}$ have the meanings indicated above and
Hal' represents chlorine or bromine,
in the presence of an acid-binding agent, for example potassium carbonate or sodium carbonate, and in the presence of an inert organic solvent, for example dimethylformamide or toluene, at temperatures between 20° and 160° C., an excess of aniline of the formula (XIII) preferably being employed (see also the preparative examples), or
(d) reacting hydrazine derivatives of the general formula

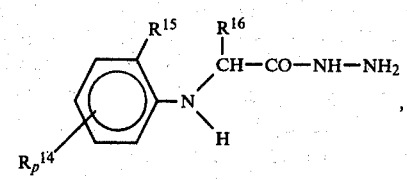
(XV)

in which
$R^{14}$, $R^{15}$, $R^{16}$ and p have the meanings indicated above,
with isocyanates or isothiocyanates of the general formula

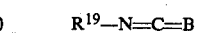 (XVI), in which
B represents oxygen or sulphur and
$R^{19}$ has the meaning indicated above,
in the presence of an organic solvent, for example an alcohol, ether or hydrocarbon, at temperatures between 0° and 80° C., and cyclizing the resulting compounds of the general formula

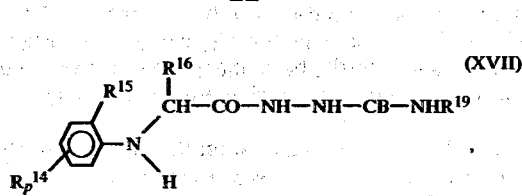

in which
B, $R^{14}$, $R^{15}$, $R^{16}$, $R^{19}$ and p have the meanings indicated above, at temperatures between 20° and 100° C. in the presence of a strong base, for example sodium hydroxide solution or potassium hydroxide solution, and in the presence of a solvent, for example ethanol or water, and reacting the resulting triazolones or triazolethiones of the general formula

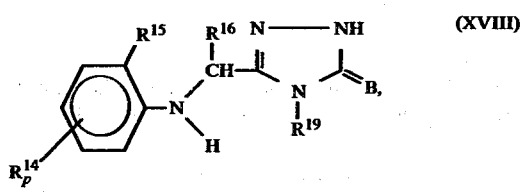

in which
B, $R^{14}$, $R^{15}$, $R^{16}$, $R^{19}$ and p have the meanings indicated above, with halides of the general formula

in which
Hal' represents chlorine or bromine and
$R^{21}$ represents the radicals of the substituent $R^{20}$, with the exception of hydrogen, in the presence of a strong base, for example sodium hydroxide solution, and in the presence of an inert organic solvent, for example toluene or methylene chloride, at temperatures between 20° and 80° C., it also being possible to carry out the reaction with phase transfer catalysts and using other alkylating reagents, for example dimethyl sulphate (see also the preparative examples), or (e) reacting hydrazine derivatives of the general formula (XV) with formic acid or acid chlorides or acid anhydrides of the general formula

or

in which
$R^{22}$ represents alkyl, haloalkyl, alkenyl, alkynyl, cycloalkyl, optionally substituted aryl or optionally substituted aralkyl, in the presence of an inert organic solvent, such as an ether or a hydrocarbon or halogenated hydrocarbon, at temperatures between 0° and 50° C. and either cyclizing the resulting compounds of the general formula

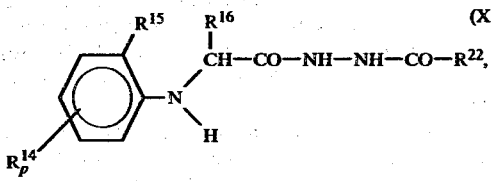

in which
$R^{14}$, $R^{15}$, $R^{16}$, $R^{22}$ and p have the meanings indicated above, with diphosphorus pentasulphide in a manner which is in itself known (see Chem. Ber. 32, 797 (1899) and J. prakt. Chemie 69, 145 (1904)) to give thiadiazole derivatives, or reacting these compounds, also in a known manner, with customary dehydrating reagents to give oxadiazole derivatives (in this context, see Elderfield, Heterocyclic Compounds, Vol. 7 (1961)), or (f) reacting hydrazine derivatives of the general formula (XV) with nitriles of the general formula

in which
$R^{23}$ represents alkyl, haloalkyl or optionally substituted aryl, in a manner which is in itself known to give triazole derivatives (see Chem. Ber. 96, 1,064 (1963)), or (g) reacting hydrazine derivatives of the general formula (XV) with imino ethers of the general formula

in which
$R^{22}$ represents alkyl, haloalkyl, alkenyl, alkynyl, cycloalkyl, optionally substituted aryl or optionally substituted aralkyl and
$R^{24}$ represents methyl or ethyl, in a manner which is in itself known, under reflux and in the presence of an inert organic solvent, for example ethanol, to give oxadiazole derivatives, or (h) reacting the anilines of the general formula (XIII) with azole-aldehydes of the general formula

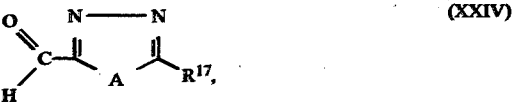

in which
$R^{17}$ has the meaning indicated above, in the presence of an inert organic solvent, for example toluene, at temperatures between 80° and 120° C., and reducing the resulting compounds of the general formula

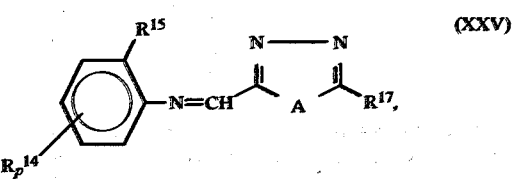

in which

A, $R^{14}$, $R^{15}$, $R^{17}$ and p have the meanings indicated above, in a generally known manner, for example by reaction with a complex hydride, such as sodium borohydride, if appropriate in the presence of a polar organic solvent, such as methanol, at temperatures between 0° and 80° C.

The compounds of the formulae (XIII) and (XIV) required as starting substances in process (c) are known, or they can be prepared by processes which are known in principle (see Helv. Chim. Acta 55, 199 et seq. (1972), Chem.Ber. 32, 797 et seq. (1899) and Chem.Ber. 96, 1,049 et seq. (1963)).

The starting substances of the formula (XV) required in process (d) have not hitherto been described in the literature. However, they can be prepared by known processes, by reacting known esters (see, inter alia, DT-OS's (German Published Specification) 2,350,944 and 2,513,730) of the general formula

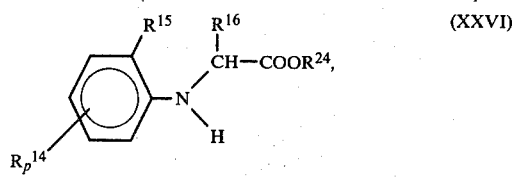

(XXVI)

in which $R^{14}$, $R^{15}$, $R^{16}$ and p have the meaning indicated above and $R^{24}$ represents methyl or ethyl, with hydrazine hydrate, preferably in the presence of an organic solvent, such as, for example, ethanol, dioxan or dimethylformamide, at temperatures between 20° and 120° C. (see also the preparative examples).

The reaction components of the formulae (XVI) and (XIX) required in process (d) are generally known compounds of organic chemistry.

The substances of the formulae (XXa), (XXb), (XXII) and (XXIII) required as reaction components in processes (e), (f) and (g) are likewise known.

The azole-aldehydes of the formula (XXIV) to be used as reaction components in process (h) are likewise known, or they can be prepared by processes which are known in principle (see Elderfield, "Heterocyclic Compounds", Volume 7 (1961) and "Advances in Heterocyclic Chemistry", Volume 9 (1968)).

The formulae (XIIa) and (XIIb) provide a general definition of the haloacetic acid chlorides and anhydrides also required as starting substances in the preparation of the acetanilides of the formula (VIII). In the formulae (XIIa) and (XIIb), $R^{18}$ preferably represents chlorine, bromine or iodine.

The haloacetic acid chlorides and anhydrides of the formulae (XIIa) and (XIIb) are generally known compounds of organic chemistry.

Preferred diluents for the reaction for the preparation of the acetanilides of the formula (VIII) are inert organic solvents. These include, as preferences, ketones, such as diethyl ketone, and in particular acetone and methyl ethyl ketone; nitriles, such as propionitrile, and in particular acetonitrile; ethers, such as tetrahydrofuran or dioxan; aliphatic and aromatic hydrocarbons, such as petroleum ether, benzene, toluene, or xylene; halogenated hydrocarbons, such as methylene chloride, carbon tetrachloride, chloroform or chlorobenzene; and esters, such as ethyl acetate.

If appropriate, the process for the preparation of acetanilides of the formula (VIII) can be carried out in the presence of an acid-binding agent (hydrogen chloride acceptor). Any of the customary acid-binding agents can be used here, preferably organic bases, such as tertiary amines, for example triethylamine, or such as pyridine, or inorganic bases, for example alkali metal hydroxides and alkali metal carbonates.

The reaction temperatures can be varied within a substantial range in carrying out the process for the preparation of the acetanilides of the formula (VIII). In general, the reaction is carried out at temperatures between 0° C. and 120° C., preferably between 20° C. and 100° C.

In carrying out the process for the preparation of the acetanilides of the formula (VIII) 1 to 1.5 moles of haloacetylating agent and 1 to 1.5 moles of acid-binding agent are preferably employed per mole of the compound of the formula (XI). Isolation of the compounds of the formula (VIII) is effected in the customary manner.

Further preferred possible acetanilides with which the compounds of the formula (I) according to the invention can be employed as antidotes are the compounds of the formulae (IX) and (X). These substances and their herbicidal activity are already known (see U.S. Pat. No. 3,442,945 and DE-OS (German Published Specification) 2,338,340).

The N,N'-bis-(haloacyl)-diaza-cycloalkanes of the formula (I) which can be used according to the invention are particularly suitable for protecting important crop plants, such as maize, soya bean, cotton, sugar beet, cereals, rice and cane sugar, from herbicidal damage by thiolcarbamates and acetanilides.

The active compound combinations according to the invention, consisting of an N,N'-bis-(halogenoacyl)-diazacycloalkane of the formula (I) and at least one herbicidally active thiolcarbamate and/or at least one herbicidally active acetanilide, exhibit a very good action against broad-leaved weeds and graminaceous weeds in numerous crops of useful plants. They can therefore be used for selectively combating weeds in numerous crops of useful plants. By weeds, in the broadest sense, there are to be understood in this context all plants which grow in locations where they are undesired.

The active compound combinations according to the invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compound combinations according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

The active compound combinations according to the invention are particularly suitable for selectively combating weeds in maize, soya beans, cotton, sugar beet, cereals, rice and cane sugar.

The antidotes which can be used according to the invention can be converted, if appropriate as a mixture with the herbicidal active compounds with which they are employed, into the customary formulations, such as solutions, emulsions, wettable powders, suspensions, powders, dusting agents, foams, pastes, soluble powders, granules, suspension-emulsion concentrates, natural and synthetic materials impregnated with active compound, very fine capsules in polymeric substances and in coating compositions, for use on seed.

These formulations are produced in known manner, for example by mixing the antidotes which can be used according to the invention, if appropriate as a mixture with the herbicidal active compounds with which they are employed, with extenders, that is, liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain between 0.1 and 95% by weight of the antidote or antidote and herbicidal active compound, preferably between 0.5 and 90%.

The antidotes which can be used according to the invention can, as stated above, also be employed as such or in the form of their formulations, as mixtures with herbicidal active compounds, finished formulations or tank mixing being possible. Mixtures with other active compounds, such as fungicides, insecticides, acaricides, nematicides, bird repellants, growth factors, plant nutrients and agents which improve soil structure are also possible.

The antidotes which can be used according to the invention or mixtures of the antidotes which can be used according to the invention and a herbicidal active compound can be employed as such, in the form of their formulations or in the use forms prepared therefrom by further dilution, such as ready-to-use solutions, suspensions, emulsions, powders and granules. They may be used in the customary manner, for example by watering, spraying, atomizing, dusting or scattering, dry dressing, moist dressing, wet dressing, slurry dressing or encrusting.

The antidotes according to the invention can be applied by methods customary for antidotes of this type. Thus, the antidotes according to the invention can be applied either before or after the herbicide, or can be applied together with the herbicide. If the herbicide is used before or after sowing, crop plants can also be protected against damage by treating the seed with the antidotes before sowing (dressing). A further possible way of using the antidotes is to apply them to the seed furrow during sowing. If the plants are seedlings, these can be treated with the antidotes before being transplanted.

When the antidotes according to the invention are employed, the customary amounts, at the location, of the particular herbicides are applied. The amounts of herbicidal active compound used vary between 0.5 and 5 kg/ha. The amount of antidote used is independent of the herbicide and of the amount of herbicidal active compound used. In general, the amounts of antidotes according to the invention applied are between 0.1 and 5 kg/ha in the case of treatment of the soil surface, preferably between 0.2 and 4 kg/ha. In the case of seed treatment, the amounts of antidotes according to the invention applied are in general between 10 and 300 g per kilogram of seed, preferably between 25 and 200 g per kilogram of seed.

The weight ratios of antidotes to herbicidal active compounds in the active compound combinations according to the invention can vary within relatively wide limits. In general, 0.05 to 1.0 part by weight, preferably 0.1 to 0.5 part by weight, of antidote of the formula (I) is present per part by weight of herbicidal active compound.

The present invention thus also provides crops protected from damage by herbicidally active thiolcarbamates or by herbicidally active acetanilides by being grown in areas in which immediately prior to and/or during the time of the growing a compound of the formula (I) was applied, alone or in admixture with a diluent or carrier.

The present invention further provides crops protected from damage by weeds by being grown in areas in which immediately prior to and/or during the time of the growing, a herbicidal composition of the present invention was applied.

It will be seen that the usual methods of providing a harvested crop may be improved by the present invention.

The good activity of the antidotes according to the invention can be seen from the Example which follows.

In this Example, the compounds indicated below are employed as comparison compounds:

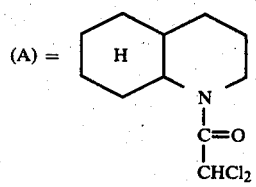

(A) =

(N-dichloroacetyl-cis/trans-decahydroquinoline)

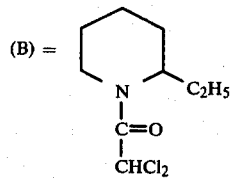

(B) =

(N-dichloroacetyl-2-ethyl-piperidine)

Furthermore, the acetanilide indicated below is employed in this Example as the herbicidal active compound:

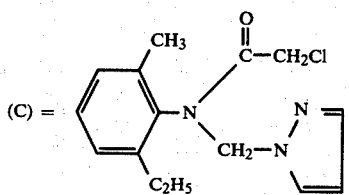

(C) =

(2-methyl-6-ethyl-N-(pyrazol-1-yl-methyl)-chloroacetanilide)

The antidotes of the formula (I) are each identified by the number, given in parentheses, of the corresponding preparative Example.

EXAMPLE A

Pre-emergence test

Solvent: 5 parts by weight of acetone
Emulsifier: 1 part by weight of alkylaryl polyglycol ether To produce a suitable preparation of active compound, 1 part by weight of herbicidal active compound or antidote, or of a mixture of antidote and herbicidal active compound, was mixed with the stated amount of solvent, the stated amount of emulsifier was added and the concentrate was diluted with water to the desired concentration.

Seeds of the test plants were sown in normal soil and, after 24 hours, watered with the herbicide preparation or antidote preparation or with the preparation of antidote and herbicidal active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0% = no action (like untreated control)
100% = total destruction.

The active compounds, amounts applied and results can be seen from the table which follows:

TABLE A

| Active Compound herbicide | Amount of active compound applied, kg or herbicide/ha | Active compound antidote | Amount of active compound applied, kg of antidote/ha | % damage to | | |
|---|---|---|---|---|---|---|
| | | | | Maize | Echinochloa | Amaranthus |
| — | — | (A) | 3 | 0 | 0 | 0 |
| — | — | (B) | 3 | 0 | 0 | 0 |
| (C) | 3 | — | — | 90 | 100 | 100 |
| (C) | 3 | (A) | 3 | 80 | 100 | 100 |
| (C) | 3 | (B) | 3 | 80 | 100 | 100 |
| — | — | (3) | 3 | 0 | 0 | 0 |
| — | — | (2) | 3 | 0 | 0 | 0 |
| (C) | 3 | (3) | 1 | 0 | 100 | 100 |
| (C) | 3 | (2) | 1 | 0 | 100 | 100 |

PREPARATIVE EXAMPLES

Example 1

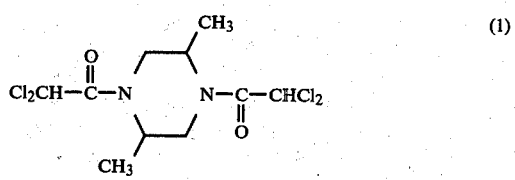

(1)

(a) 29.4 g (0.2 mol) of dichloroacetyl chloride were added dropwise to a solution of 22.8 g (0.2 mol) of 2,5-dimethyl-piperazine in 150 ml of toluene at 20° C., while stirring. The mixture was subsequently stirred at 20° C. for 5 hours. Thereafter, the precipitate which had formed was filtered off and recrystallized twice from toluene. 8 g (24% of theory) of N,N'-bis-(dichloroacetyl)-2,5-dimethyl-piperazine were obtained in this manner in the form of colorless crystals of melting point 215° C.

(b) 29.4 g (0.2 mol) of dichloroacetyl chloride were added dropwise to a solution of 22.8 g (0.2 mol) of 2,5-dimethyl-piperazine in 150 ml of acetonitrile at 20° C., while stirring. The reaction mixture was allowed to react subsequently at 20° C. for 5 hours and was then poured into 300 ml of water and the precipitate obtained was filtered off and recrystallized from toluene. 12 g (36% of theory) of N,N'-bis-(dichloroacetyl)-2,5-dimethylpiperazine were obtained in this manner in the form of colorless crystals of melting point 214° C.

The compounds of the formula (I) listed in Table 1 below were prepared in an analogous manner:

melting point 67° C. were obtained in the form of colorless crystals.

(2) The reaction mixture was cooled to 0° C. and filtered and the residue on the filter was rinsed with 10 ml of cold ethyl acetate. 50 g (1.4 mol) of dry hydrogen chloride were passed into the filtrate at 0° to −10° C. The hydrochloride salts which had precipitated were then filtered off and rinsed with 50 ml of cold ethyl acetate and the solid residue was partitioned between 0.5 liter of ethyl acetate and 0.5 liter of aqueous sodium hydroxide solution with a pH value of 12. The organic phase was separated off, washed twice with 0.5 liter of sodium chloride solution each time, dried over sodium sulphate and evaporated in vacuo. 60 ml of benzine were added to the colorless oily residue, whereupon it crystallized. 220.2 g (72% of theory) of 2,6-diethyl-N-(pyrazol-1-yl)methyl)-chloroacetanilide of melting

TABLE 1

$$R^3R^4CH-CO-N \underset{Q}{\overset{R^6 \quad R^5}{\diagup\diagdown}} N-CO-CHR^1R^2 \quad (I)$$

| Example No. | $R^1$ | $R^2$ | $R^3$ | $R^4$ | $R^5$ | $R^6$ | Q | Melting point/°C. |
|---|---|---|---|---|---|---|---|---|
| 2 | $CH_3$ | Cl | $CH_3$ | Cl | H | $CH_3$ | $-CH_2-CH(CH_3)-$ | 167 |
| 3 | Cl | Cl | Cl | Cl | H | H | $-(CH_2)_3-$ | 130 |
| 4 | $CH_3$ | Cl | $CH_3$ | Cl | H | H | $-(CH_2)_3-$ | partly crystalline |
| 5 | Cl | Cl | Cl | Cl | H | H | $-CH_2-CH_2-$ | 217 |
| 6 | $CH_3$ | Cl | $CH_3$ | Cl | H | H | $-CH_2-CH_2-$ | |
| 7 | Cl | Cl | Cl | Cl | $CH_3$ | H | $-CH_2-CH(CH_3)-$ | 225 |
| 8 | Cl | $CH_3$ | Cl | $CH_3$ | $CH_3$ | H | $-CH_2-CH(CH_3)-$ | 137 |
| 9 | Cl | Cl | Cl | Cl | $CH_3$ | H | $-CH_2-CH_2-$ | 160 |

EXAMPLE (VI-1)

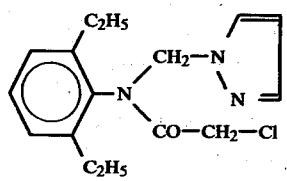

A mixture of 68 g (1 mol) of pyrazole and 106 g (1.05 mol) of triethylamine in 150 ml of anhydrous ethyl acetate were added to 274.2 g (1 mol) of 2,6-diethyl-N-chloromethyl-chloroacetanilide in 250 ml of anhydrous ethyl acetate, while stirring, during which the temperature rose to 30° C. The mixture was subsequently stirred for 1 hour at room temperature. There were two possibilities for working up:

(1) The reaction mixture was filtered and the filtrate was washed with water until neutral, dried over sodium sulphate and evaporated in vacuo. After fractional crystallization with ligroin, 171.2 g (56% of theory) of 2,6-diethyl-N-(pyrazol-1-yl-methyl)-chloroacetanilide of point 67° C. were obtained in the form of colorless crystals.

The compounds listed in the Table below were prepared in an analogous manner:

TABLE 2

$$\underset{Y_n}{\overset{X}{\text{Ar}}}-N\underset{CO-CH_2-Z}{\overset{CH_2-R}{\diagup}} \quad (VI)$$

| Example No. | X | $Y_n$ | Z | R | Melting point (°C.) |
|---|---|---|---|---|---|
| VI-2 | $C_2H_5$ | 6-$C_2H_5$ | Cl | 1,2,4-Triazol-1-yl | 112 |
| VI-3 | i-$C_3H_7$ | 6-i-$C_3H_7$ | Cl | Pyrazol-1-yl | 134 |
| VI-4 | $CH_3$ | 6-$C_2H_5$ | Cl | 1,2,4-Triazol-1-yl | 92 |
| VI-5 | $CH_3$ | 6-$C_2H_5$ | Cl | Pyrazol-1-yl | 57 |
| VI-6 | $C_2H_5$ | 4,6-$(CH_3)_2$ | Cl | Pyrazol-1-yl | 32 |
| VI-7 | $CH_3$ | 4,6-$(CH_3)_2$ | Cl | Pyrazol-1-yl | 92 |
| VI-8 | $C_2H_5$ | 4-$CH_3$, 6-$C_2H_5$ | Cl | Pyrazol-1-yl | 78 |

TABLE 2-continued (VI)

$$\underset{Y_n}{\text{Ar}}\begin{array}{c} X \\ \diagdown \\ N \\ \diagup \\ \end{array}\begin{array}{c} CH_2-R \\ \\ CO-CH_2-Z \end{array}$$

| Example No. | X | $Y_n$ | Z | R | Melting point (°C.) |
|---|---|---|---|---|---|
| VI-9 | i-C$_3$H$_7$ | 6-i-C$_3$H$_7$ | Cl | 1,3,4-Triazol-1-yl | 196 |
| VI-10 | i-C$_3$H$_7$ | 6-i-C$_3$H$_7$ | Cl | 1,2,4,-Triazol-1-yl | 138 |
| VI-11 | C$_2$H$_5$ | 6-C$_2$H$_5$ | Cl | Pyrrol-1-yl | Oil |
| VI-12 | i-C$_3$H$_7$ | — | Cl | 1,2,4-Triazol-1-yl | 118 |
| VI-13 | CH$_3$ | 6-C$_2$H$_5$ | Cl | 1,2,3,4-Tetrazol-1-yl | Oil |
| VI-14 | i-C$_3$H$_7$ | — | Cl | Pyrazol-1-yl | Oil |
| VI-15 | C$_2$H$_5$ | — | Cl | 1,2,4-Triazol-1-yl | 81 |
| VI-16 | CH$_3$ | 6-CH$_3$ | Cl | Pyrazol-1-yl | 82 |
| VI-17 | CH$_3$ | 6-CH$_3$ | Cl | 1,2,4-Triazol-1-yl | 110 |
| VI-18 | CH$_3$ | 5-CH$_3$ | Cl | 1,2,4-Triazol-1-yl | Oil |
| VI-19 | CH$_3$ | — | Cl | Pyrazol-1-yl | 56 |
| VI-20 | CH$_3$ | — | Cl | 1,2,4-Triazol-1-yl | 88 |
| VI-21 | CH$_3$ | 5-CH$_3$ | Cl | Pyrazol-1-yl | Oil |
| VI-22 | CH$_3$ | 3-CH$_3$ | Cl | 1,2,4-Triazol-1-yl | 114 |
| VI-23 | CH$_3$ | 3-CH$_3$ | Cl | Pyrazol-1-yl | 102 |
| VI-24 | C$_2$H$_5$ | 6-CH$_3$ | Cl | Pyrazol-1-yl (xHCl) | 87 |
| VI-25 | C$_2$H$_5$ | 6-C$_2$H$_5$ | Cl | Pyrazol-1-yl (xHCl) | 67 |
| VI-26 | C$_2$H$_5$ | 6-C$_2$H$_5$ | Cl | 3,5-Dimethyl-pyrazol-1-yl | 111 |
| VI-27 | C$_2$H$_5$ | 6-C$_2$H$_5$ | Cl | Bromo-methyl-pyrazolyl | 145 |
| VI-28 | C$_2$H$_5$ | 6-C$_2$H$_5$ | Cl | 3-Chloro-1,2,4-triazol-1-yl | 110 |
| VI-29 | CH$_3$ | 6-C$_2$H$_5$ | Cl | 3,5-Dimethyl-pyrazol-1-yl | 90 |
| VI-30 | C$_2$H$_5$ | 6-C$_2$H$_5$ | Cl | 3-Methyl-pyrazol-1-yl | 89 |
| VI-31 | C$_2$H$_5$ | 6-CH$_3$ | Cl | 3-Methyl-pyrazol-1-yl | 113 |
| VI-32 | C(CH$_3$)$_3$ | — | Cl | Pyrazol-1-yl | Oil |
| VI-33 | C(CH$_3$)$_3$ | — | Cl | 1,2,4-Triazol-1-yl | 118 |
| VI-34 | C$_2$H$_5$ | 6-CH$_3$ | Cl | Bromo-methyl-pyrazolyl | 80 |
| VI-35 | CH$_3$ | 6-C$_2$H$_5$ | Cl | 4-Chloro-pyrazol-1-yl | 91 |
| VI-36 | CH$_3$ | 6-C$_2$H$_5$ | Cl | 3-Chloro-1,2,4-triazol-1-yl | 121 |
| VI-37 | C$_2$H$_5$ | 6-CH$_3$ | Cl | 2,4,5-Trichloro-imidazol-1-yl | 158 |
| VI-38 | C$_2$H$_5$ | 6-C$_2$H$_5$ | Cl | 4-Chloro-pyrazol-1-yl | 110 |
| VI-39 | C$_2$H$_5$ | 6-C$_2$H$_5$ | Cl | 1,2,3,4-Tetrazol-1-yl | 110 |
| VI-40 | C$_2$H$_5$ | 6-C$_2$H$_5$ | Br | Pyrazol-1-yl | 68 |
| VI-41 | CH$_3$ | 6-C$_2$H$_5$ | Br | Pyrazol-1-yl | 67 |
| VI-42 | C$_2$H$_5$ | 6-C$_2$H$_5$ | Cl | Imidazol-1-yl | Oil |
| VI-43 | C$_2$H$_5$ | 6-C$_2$H$_5$ | Br | 1,2,4-Triazol-1-yl | 90 |
| VI-44 | CH$_3$ | 6-C$_2$H$_5$ | Br | 1,2,4-Triazol-1-yl | 78 |

EXAMPLE (VII-1)

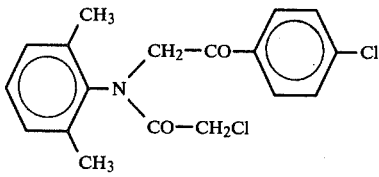

16 ml (0.2 mol) of chloroacetyl chloride were added dropwise to a solution of 18.5 g (0.068 mol) of 2,6-dimethyl-N-(4-chloro-benzoylmethyl)-aniline in 150 ml of benzene. Thereafter, the mixture was stirred under reflux for 15 hours and was concentrated by distilling off the solvent and the excess chloroacetyl chloride in vacuo. The residue was triturated with a mixture of ether/petroleum ether (1:3) and the crystalline residue formed was filtered off and dried. 17.7 g (75% of theory) of 2,6-dimethyl-N-(4-chlorobenzoylmethyl)-chloroacetanilide of melting point 128° C. were obtained.

EXAMPLE (VII-2)

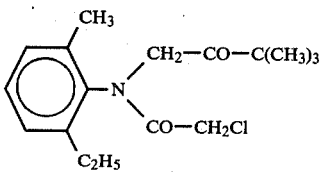

23.3 g (0.1 mol) of 2-ethyl-6-methyl-N-pivaloylmethyl-aniline were dissolved in 100 ml of benzene, and 24 ml (0.3 mol) of chloroacetyl chloride were added. Thereafter, the mixture was stirred under reflux for 15 hours and was concentrated by distilling off the solvent and the excess chloroacetyl chloride in vacuo. The oily residue was stirred with petroleum ether, the mixture was decanted, the product phase was stirred with active charcoal and filtered and the filtrate was concentrated in vacuo. The residue was stirred with n-hexane and the resulting solid was filtered off and dried. 13.7 g (45% of theory) of 2-ethyl-6-methyl-N-pivaloylmethyl-chloroacetanilide of melting point 86° C. were obtained.

The compounds listed in Table 3 below were also prepared by the method described in Examples (VII-1) and (VII-2):

TABLE 3
(VII)
| Example No. | $R_m^{10}$ | $R^{11}$ | $R^{12}$ | $R^{13}$ | Melting point (°C.) or refractive index |
|---|---|---|---|---|---|
| VII-3 | 2-CH$_3$ | H | H |  | 138 |
| VII-4 | 2-CH$_3$ | H | H |  | 140 |
| VII-5 | 2,6-(C$_2$H$_5$)$_2$ | H | H |  | 134 |
| VII-6 | 2,6-(C$_2$H$_5$)$_2$ | H | H |  | 116 |
| VII-7 | 2-Cl | H | H |  | 124 |
| VII-8 | 2,6-(CH$_3$)$_2$ | H | H |  | 100 |
| VII-9 | 4-Cl | H | H |  | 114 |
| VII-10 | 2,6-(CH$_3$)$_2$ | CH$_3$ | H | CH$_3$ | 104 |
| VII-11 | 2,6-(i-C$_3$H$_7$)$_2$ | H | H |  | 200 |
| VII-12 | 2,6-(C$_2$H$_5$)$_2$, 4-CH$_3$ | H | H |  | 112 |
| VII-13 | 2,6-(i-C$_3$H$_7$)$_2$ | H | H |  | 140 |
| VII-14 | 2,6-(CH$_3$)$_2$ | H | H |  | 90 |
| VII-15 | 2-C$_2$H$_5$, 6-CH$_3$ | H | H |  | 70 |
| VII-16 | 2,6-(CH$_3$)$_2$ | H | H |  | 114 |
| VII-17 | 2-C$_2$H$_5$, 4,6-(CH$_3$)$_2$ | H | H |  | $n_D^{20} = 1.5680$ |
| VII-18 | 2,6-(CH$_3$)$_2$ | H | H |  | 104 |

TABLE 3-continued
| Example No. | $R_m{}^{10}$ | $R^{11}$ | $R^{12}$ | $R^{13}$ | Melting point (°C.) or refractive index |
|---|---|---|---|---|---|
| VII-19 | 2,4,6-(CH$_3$)$_3$ | H | H |  | 134 |
| VII-20 | 2,4,6-(CH$_3$)$_3$ | H | H |  | $n_D{}^{20} = 1.5610$ |
| VII-21 | 2,6-(CH$_3$)$_2$ | H |  |  | 149 |
| VII-22 | 2,6-(CH$_3$)$_2$ | H | CH$_3$ | 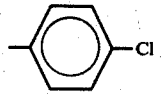 | 84 |
The compounds listed in Table 4 below could be obtained in an analogous manner.
TABLE 4
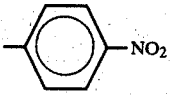
| Example No. | $R_m{}^{10}$ | $R^{11}$ | $R^{12}$ | $R^{13}$ |
|---|---|---|---|---|
| VII-23 | 3,5-(CF$_3$)$_2$ | H | H | 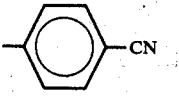 |
| VII-24 | 2,6-(CH$_3$)$_2$ | H | H | 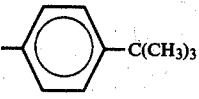 |
| VII-25 | 2,6-(CH$_3$)$_2$ | H | H | 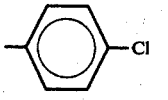 |
| VII-26 | 2,6-(CH$_3$)$_2$ | H | H | 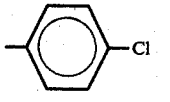 |
| VII-27 | 2,6-(CH$_3$)$_2$, 4-SC$_2$NH$_2$ | H | H |  |
| VII-28 | 2-Cl, 6-CH$_3$ | H | H |  |

TABLE 4-continued
(VII)
$$\text{structure with } R_m{}^{10}\text{-phenyl-N(CO-CH}_2\text{Cl)-C(R}^{11})(R^{12})\text{-CO-R}^{13}$$
| Example No. | $R_m{}^{10}$ | $R^{11}$ | $R^{12}$ | $R^{13}$ | |
|---|---|---|---|---|---|
| VII-29 | 2-C$_2$H$_5$, 6-CH$_3$ | CH$_3$ | CH$_3$ |  | |
| VII-30 | 2-C$_2$H$_5$, 6-CH$_3$ | CH$_3$ | CH$_3$ |  | |
| VII-31 | 2-C$_2$H$_5$, 6-CH$_3$ | CH$_3$ | CH$_2$ | 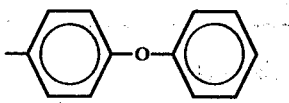 | |
| VII-32 | 2-C$_2$H$_5$, 6-CH$_3$ | CH$_3$ | CH$_3$ | 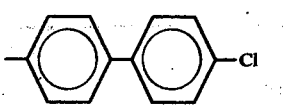 | |
| VII-33 | 2-C$_2$H$_5$, 6-CH$_3$— | CH$_3$ | CH$_3$ | 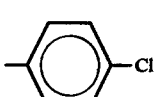 | |
| VII-34 | 2-C$_2$H$_5$, 6-CH$_3$ | H | CH$_3$ | 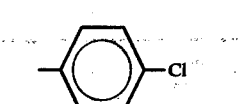 | |
| VII-35 | 2-C$_2$H$_5$, 6-CH$_3$ | H | CH$_3$ |  | |
| VII-36 | 2,6-(CH$_3$)$_2$ | H | 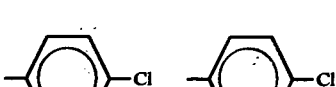 | 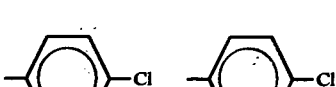 | |
| VII-37 | 2,6-(CH$_3$)$_2$ | H |  |  | |
| VII-38 | 2,6-(CH$_3$)$_2$ | H |  |  | |
| VII-39 | 2,6-(CH$_3$)$_2$ | H |  |  | |

TABLE 4-continued (VII)

[Structure VII shown with R¹¹, R¹², CO—R¹³, CO—CH₂Cl, N, phenyl ring, R$_m^{10}$]

| Example No. | R$_m^{10}$ | R¹¹ | R¹² | R¹³ |
|---|---|---|---|---|
| VII-40 | 2,6-(CH₃)₂ | H | -⟨phenyl⟩-Cl | -⟨phenyl⟩ |
| VII-41 | 2,6-(CH₃)₂ | H | CH₃ | -⟨phenyl⟩-Cl |

EXAMPLE (VIII-1)

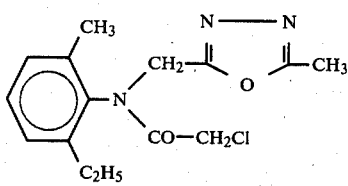

16.3 g (0.07 mol) of 2-ethyl-6-methyl-N-[(2-methyl-1-3,4-oxadiazol-5-yl)-methyl]-aniline and 6 g (0.076 mol) of anhydrous pyridine in 100 ml of absolute tetrahydrofuran were heated to the boiling point, while stirring, and a solution of 8 g (0.07 mol) of chloroacetyl chloride in 20 ml of tetrahydrofuran was added dropwise. When the dropwise addition had ended, the mixture was subsequently stirred for 10 minutes and was concentrated by distilling off the solvent, and the residue was stirred with 150 ml of water. The reaction product which crystallized out was filtered off, washed with water and dried. 18.7 g (87% of theory) of beige-colored crystals of 2-ethyl-6-methyl-N-[(2-methyl-1,3,4-oxadiazol-5-yl)-methyl]-chloroacetanilide of melting point 67° to 70° C. were obtained.

Preparation of the starting material

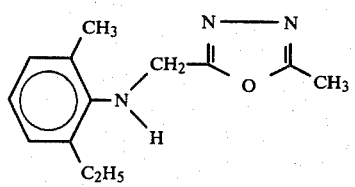

A mixture of 101.2 g (0.76 mol) of 2-ethyl-6-methylaniline, 40 g (0.3 mol) of 2-methyl-5-chloromethyl-1,3,4-oxadiazole, 41.4 g (0.4 mol) of powdered potassium carbonate and 76 ml of dimethylformamide was heated to 100° C. for 5 hours, while stirring. Thereafter, the reaction mixture was filtered and the filtrate was diluted with methylene chloride and washed several times with water. The methylene chloride phase was dried over sodium sulphate and concentrated in vacuo by distilling off the solvent. The residue was distilled in vacuo. 46.8 g (67.5% of theory) of a yellowish oil consisting of 2-ethyl-6-methyl-N-[(2-methyl-1,3,4-oxadiazol-5-yl)-methyl]-aniline of boiling point 140° to 142° C./0.1 mm Hg with a purity of 94% (determined by gas chromatography) were obtained.

EXAMPLE (VIII-2)

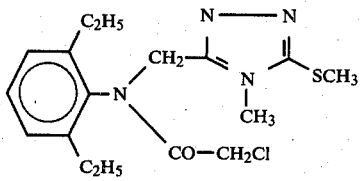

5 g (0.017 mol) of 2,6-diethyl-N-[(1-methyl-2-methylthio-1,3,4-triazol-5-yl)-methyl]-aniline and 1.6 g (0.02 mol) of pyridine were stirred in 100 ml of absolute tetrahydrofuran and 2.3 g (0.02 mol) of chloroacetyl chloride were added dropwise at room temperature, whereupon the temperature rose to about 30° C. The mixture was stirred for 2 hours and was partly concentrated by distilling off the solvent, and water was added. The product which crystallized out was filtered off, dried and recrystallized from diisopropyl ether/ethyl acetate. 5 g (80% of theory) of 2,6-diethyl-N-[(1-methyl-2-methylthio-1,3,4-triazol-5-yl)-methyl]-chloroacetanilide of melting point 121° to 123° C. were obtained.

Preparation of the precursors

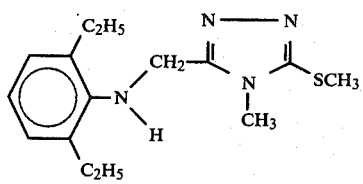

(a)

13.9 g (0.05 mol) of 2,6-diethyl-N-[(1-methyl-2-thiono-1,3,4-triazol-5-yl)-methyl]-aniline were stirred rapidly in a two-phase mixture of 150 ml of toluene and 40 ml of 50% strength sodium hydroxide solution, with the addition of 1.5 g of triethyl-benzyl ammonium chloride (TEBA) as the catalyst, at room temperature and 6.3 g (0.05 mol) of dimethyl sulphate were added dropwise, whereupon the temperature rose to about 35° C. The mixture was stirred for 5 hours and the toluene phase was separated off, washed several times with water, dried over sodium sulphate and concentrated by distilling off the solvent. The oil which remained was made to crystallize by adding petroleum ether. After recrystallization from petroleum ether, 6.7 g (40% of theory) of 2,6-diethyl-N-[(1-methyl-2-methylthio-1,3,4-triazol-5-yl)-methyl]-aniline of melting point 65° to 67° C. were obtained.

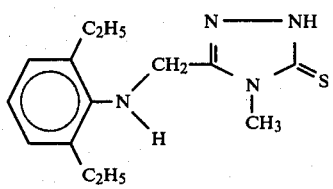 (b)

29.6 g (0.1 mol) of 1-methyl-4-[(2,6-diethyl-anilino)acetyl]-thiosemicarbazide were suspended in 150 ml of ethanol and, after adding 7 g of potassium hydroxide in 20 ml of water, the mixture was heated under reflux for 1 hour. Thereafter, most of the solvent was distilled off and 250 ml of water were added to the residue. After acidifying the mixture to pH 5 with glacial acetic acid, the precipitate formed was filtered off and washed thoroughly with water. After drying, 27 g (97% of theory) of 2,6-diethyl-N-[(1-methyl-2-thiono-1,3,4-triazol-5-yl)-methyl]-aniline of melting point 117° to 121° C. were obtained.

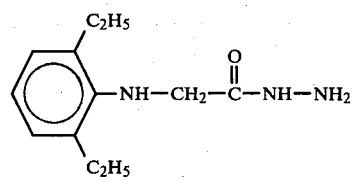 (c)

44.2 g (0.2 mol) of 2,6-diethyl-anilino-acetic acid hydrazide and 14.8 g (0.2 mol) of methyl isothiocyanate were dissolved in 250 ml of ethanol and the solution was heated to the reflux temperature for one hour. After subsequent cooling to room temperature, the precipitate which had formed was filtered off and rinsed twice with 50 ml of ethanol each time. After drying, 46 g (78% of theory) of 1-methyl-4-[2,6-diethyl-anilino)-acetyl]thiosemicarbazide were obtained in the form of a colorless crystalline substance of melting point 166° C.

(d)

58.7 g (0.25 mol) of 2,6-diethyl-anilino-acetic acid ethyl ester and 25 g of hydrazine hydrate were left to stand in 200 ml of ethanol for 24 hours. Thereafter, the mixture was concentrated by distilling off the solvent and the residue was extracted by stirring with water. After drying, 50.5 g (91% of theory) of colorless crystals of 2,6-diethyl-anilino-acetic acid hydrazide of melting point 71° to 73° C. were obtained.

Those compounds listed by means of their formulae in Table 5 were obtained in a corresponding manner.

TABLE 5

(VIII)

| Example No. | R¹⁶ | R¹⁷ | R¹⁵ | Rₚ¹⁴ | A | R¹⁸ | Melting point (°C.) |
|---|---|---|---|---|---|---|---|
| VIII-3 | H | CH₃ | C₂H₅ | 6-C₂H₅ | O | Cl | 79–82 |
| VIII-4 | H | CH₃ | CH₃ | 6-CH₃ | O | Cl | 91–93 |
| VIII-5 | H | CH₃ | C(CH₃)₃ | — | O | Cl | 102-04 |
| VIII-6 | H | —S—CH₂—CH=CH₂ | C₂H₅ | 6-C₂H₅ | \N/ CH₃ | Cl | 67-70° |
| VIII-7 | H | —S—CH₂—(C₆H₄-F) | CH₃ | 6-C₃H₅ | \N/ CH₃ | Cl | 115-20 |
| VIII-8 | H | C₂H₅ | CH₃ | 6-C₂H₅ | O | Cl | 57–59 |
| VIII-9 | H | C₂H₅ | C₂H₅ | 6-C₂H₅ | O | Cl | 43–47 |
| VIII-10 | H | i-C₃H₇ | CH₃ | 6-C₂H₅ | O | Cl | viscous oil |

TABLE 5-continued

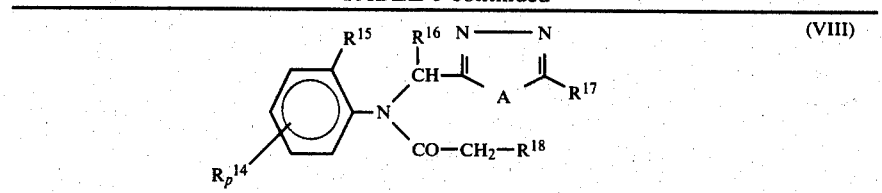

| Example No. | R¹⁶ | R¹⁷ | R¹⁵ | R_p¹⁴ | A | R¹⁸ | Melting point (°C.) |
|---|---|---|---|---|---|---|---|
| VIII-11 | H | CH₃ | CH₃ | 3-CH₃ | (N,N-dimethyl-2,3-dimethylanilino) | Cl | glass-like solid |
| VIII-12 | H | CH₃ | C₂H₅ | 6-C₂H₅ | O | Br | 80° |
| VIII-13 | H | CH₃ | CH₃ | 6-C₂H₅ | O | Br | 92–94° C. |
| VIII-14 | H | CH₃ | i-C₃H₇ | 6-i-C₃H₇ | O | Cl | 135–37° |

The starting materials listed by means of their formulae in Table 6 which follows were obtained by one or more of the processes described in the present specification.

It will be understood that the specification and examples are illustrative, but not limitative of the present invention and that other embodiments within the spirit

TABLE 6

| Example No. | R¹⁶ | R¹⁷ | R¹⁵ | R_p¹⁴ | A | Melting point or (°C.) refractive index |
|---|---|---|---|---|---|---|
| XI-1 | H | CH₃ | C₂H₅ | 6-C₂H₅ | O | $n_D^{22} = 1.540$ |
| XI-2 | H | CH₃ | CH₃ | 6-C₂H₅ | O | $n_D^{22} = 1.547$ |
| XI-3 | H | CH₃ | CH₃ | 6-CH₃ | O | $n_D^{22} = 1.552$ |
| XI-4 | H | CH₃ | —(CH₃)₃ | — | O | 52–55 |
| XI-5 | H | CH₃ | i-C₃H₇ | 6-i-C₃H₇ | O | 96–99 |
| XI-6 | H | C₂H₅ | C₂H₅ | 6-C₂H₅ | O | $n_D^{22} = 1.534$ |
| XI-7 | H | C₂H₅ | CH₃ | 6-C₂H₅ | O | $n_D^{21} = 1.542$ |
| XI-8 | H | i-C₃H₇ | CH₃ | 6-C₂H₅ | O | $n_D^{21} = 1.531$ |
| XI-9 | H | SCH₃ | C₂H₅ | 6-C₂H₅ | N—CH₃ | |
| XI-10 | H | S—CH₂—CH=CH₂ | C₂H₅ | 6-C₂H₅ | N—CH₃ | $n_D^{21} = 1.577$ |
| XI-11 | H | S—CH₂—(2-F-phenyl) | CH₃ | 6-C₂H₅ | N—CH₃ | viscous oil |
| XI-12 | H | CH₃ | CH₃ | 3-CH₃ | N—(2,3-dimethylphenyl) | 142–143 |

What is claimed is:

1. Method for protecting maize from damage by herbicidally active acetanilides of the formula

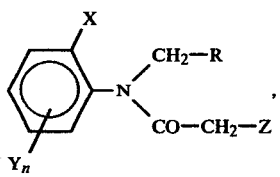

wherein
R represents pyrazol-1-yl -or pyrazol-1-yl substituted by halogen or alkyl with 1 to 4 carbon atoms,
X and Y are identical or different and represent alkyl with 1 to 4 carbon atoms,
Z represents chlorine and
n represents 0,1 or 2, and herbicidally active acid addition salts and metal salt complexes thereof, which comprises applying to the plants or their habitat an antidotally effective amount of N,N'-bis-(haloacyl)-diazacycloalkane compound of the formula

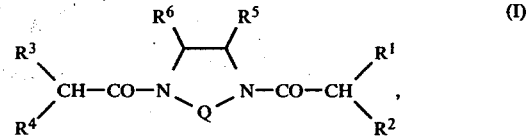

wherein
$R^1$ is methyl or chlorine;
$R^2$ is chlorine;
$R^3$ is methyl or chlorine;
$R^4$ is chlorine;
$R^5$ is hydrogen or alkyl with 1 or 2 carbon atoms;
$R^6$ is hydrogen or alkyl with 1 or 2 carbon atoms; and
Q is an alkylene chain which has 2 or 3 carbon atoms and can be mono-substituted by methyl.

2. Method as claimed in claim 1 wherein the active compound is applied to an area of agriculture in an amount of from 0.1 to 5 kg per hectare.

3. Method as claimed in claim 1 wherein the active compound is applied to seed in an amount of 10 to 200 per gram kg of seed.

4. Herbicidal composition for use in maize comprising a herbicidally active compound selected from acetanilide herbicides of the formula

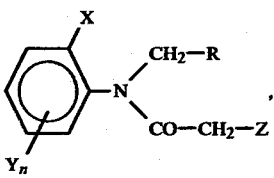

in which
R represents pyrazol-1-yl or pyrazol-1-yl substituted by halogen or alkyl with 1 to 4 carbon atoms,
X and Y are identical or different and represent alkyl with 1 to 4 carbon atoms,
Z represents halogen and
n represents 0,1 or 2, and herbicidally active acid addition salts and metal salt complexes thereof, and as an antidote, an N,N'-bis-(haloacyl)-diazacycloalkane compound of the formula $$\begin{array}{c} R^6 \quad R^5 \\ R^3 \diagdown \diagup \diagdown \diagup R^1 \\ CH-CO-N \diagdown_Q\diagup N-CO-CH \\ R^4 \diagup \qquad \diagdown R^2 \end{array} \quad (I)$$

wherein
$R^1$ is methyl or chlorine;
$R^2$ is chlorine;
$R^3$ is methyl or chlorine;
$R^4$ is chlorine;
$R^5$ is hydrogen or alkyl with 1 or 2 carbon atoms;
$R^6$ is hydrogen or alkyl with 1 or 2 carbon atoms; and
Q is an alkylene chain which has 2 or 3 carbon atoms and can be mono-substituted by methyl.

5. Herbicidal composition as claimed in claim 4 containing from 0.05 to 1 part by weight of the compound of formula (I) per part by weight of said herbicidally active compound.

6. Herbicidal composition as claimed in claim 4 containing from 0.1 to 0.5 part by weight of the compound of formula (I) per part by weight of said herbicidally active compound.

7. Method of combating weeds in maize comprising applying to the weeds or their habitat a composition as claimed in claim 4.

8. Method as claimed in claim 7 wherein the composition is applied at a rate corresponding to 0.5 to 5 kg of acetanilides per hectare.

9. Herbicidal composition as claimed in claim 4 wherein said antidote is N,N'-bis-(dichloroacetyl)-2,5-dimethyl-piperazine.

10. Herbicidal composition as claimed in claim 4 wherein said antidote is N,N'-bis-(alpha-chloropropionyl)-2,5-dimethyl-piperazine.

11. Herbicidal composition as claimed in claim 4 wherein said antidote is N,N'-bis-(dichloroacetyl)-hexahydro-1,4-diazepine.

12. Herbicidal composition as claimed in claim 4 wherein said antidote is N,N'-bis-(alpha-chloropropionyl)-hexahydro-1,4-diazepine.

13. Herbicidal composition as claimed in claim 4 wherein said antidote is N,N'-bis-(alpha-chloropropionyl)-piperazine.

14. Herbicidal composition as claimed in claim 4 wherein said antidote compound is selected from
N,N'-bis(dichloroacetyl)-2,5-dimethylpiperazine;
N,N'-bis-(alpha-chloropropionyl)-2,5-dimethylpiperazine;
N,N'-bis-(dichloroacetyl)-hexahydro-1,4-diazepine;
N,N'-bis-(alpha-chloropropionyl)-hexahydro-1,4-diazepine; and
N,N'-bis-(alpha-chloropropionyl)-piperazine.

15. Method as claimed in claim 7 wherein said antidote compound is selected from
N,N'-bis(dichloroacetyl)-2,5-dimethylpiperazine;
N,N'-bis-(alpha-chloropropionyl)-2,5-dimethylpiperazine;
N,N'-bis-(dichloroacetyl)-hexahydro-1,4-diazepine;
N,N'-bis-(alpha-chloropropionyl)-hexahydro-1,4-diazepine; and
N,N'-bis-(alpha-chloropropionyl)-piperazine.

* * * * *